United States Patent [19]

Rothfuss

[11] Patent Number: 4,485,953
[45] Date of Patent: Dec. 4, 1984

[54] SURGICAL STAPLING INSTRUMENT AND CARTRIDGE THEREFOR

[75] Inventor: Robert G. Rothfuss, Bellevue, Ky.

[73] Assignee: Senco Products, Inc., Cincinnati, Ohio

[21] Appl. No.: 365,544

[22] Filed: Apr. 5, 1982

[51] Int. Cl.³ .............................................. A61B 17/04
[52] U.S. Cl. .................................. 227/19; 128/334 R; 200/339; 200/340; 227/143; 227/DIG. 1
[58] Field of Search .................. 128/334 R, 335, 337, 128/321; 206/339, 340; 227/DIG. 1, 19, 443

[56] References Cited

U.S. PATENT DOCUMENTS

| | | | |
|---|---|---|---|
| 1,836,944 | 12/1931 | Vogel | 227/143 |
| 3,278,104 | 10/1966 | Becht et al. | 227/130 |
| 3,278,107 | 10/1966 | Rygg | 227/143 |
| 3,326,216 | 6/1967 | Wood | 128/325 |
| 3,439,523 | 4/1969 | Wood | 72/410 |
| 3,618,842 | 11/1971 | Bryan | 227/138 |
| 3,631,707 | 1/1972 | Miller | 72/410 |
| 3,638,847 | 2/1972 | Noiles et al. | 227/120 |
| 3,650,453 | 3/1972 | Smith, Jr. | 227/138 |
| 3,713,533 | 1/1973 | Reimels | 206/339 |
| 3,819,100 | 6/1974 | Noiles et al. | 227/19 |
| 3,867,944 | 2/1975 | Samuels | 128/325 |
| 3,873,016 | 3/1975 | Fishbein | 227/19 X |
| 4,043,504 | 8/1977 | Hueil et al. | 227/116 |
| 4,076,120 | 2/1978 | Carroll et al. | 206/339 |
| 4,196,836 | 4/1980 | Becht | 227/110 |
| 4,361,229 | 11/1982 | Mericle | 206/339 |
| 4,412,539 | 11/1983 | Jarvik | 227/DIG. 1 |

Primary Examiner—Paul A. Bell
Attorney, Agent, or Firm—Frost & Jacobs

[57] ABSTRACT

A surgical stapling system comprising a surgical stapling instrument and a staple-carrying cartridge therefor. The surgical stapling instrument comprises a pliers-like instrument having upper and lower handles pivotally joined together. The upper handle has an elongated front portion terminating in an anvil. A staple former is slidably mounted on the front portion and is axially shiftable thereon by the lower handle between a normal or retracted position and a staple forming position. Co-operating leaf springs are mounted on each of the handles to normally urge the handles apart and the former to its retracted position. Portions of the leaf springs cooperate to lock the former in a staple gripping position. The cartridge comprises an elongaged member having a plurality of transverse slots formed in its upper surface and in parallel spaced relationship. A surgical staple of inverted U-shaped configuration, having downwardly depending legs and a crown portion extending therebetween, is located in each transverse slot. Each transverse slot is of a length such that its ends frictionally engage the legs of the surgical staple therein. A longitudinal groove is formed in the upper surface of the cartridge, extending the length of the cartridge and intersecting the transverse slots therein. The longitudinal groove is of a width and depth such as to receive the surgical stapling instrument nose portion with the staple former above and the anvil surface below the crown of an individual staple in the cartridge, so that the crown of the staple may be engaged between the instrument former and the anvil surface and extracted from the cartridge by the surgical stapling instrument.

28 Claims, 35 Drawing Figures

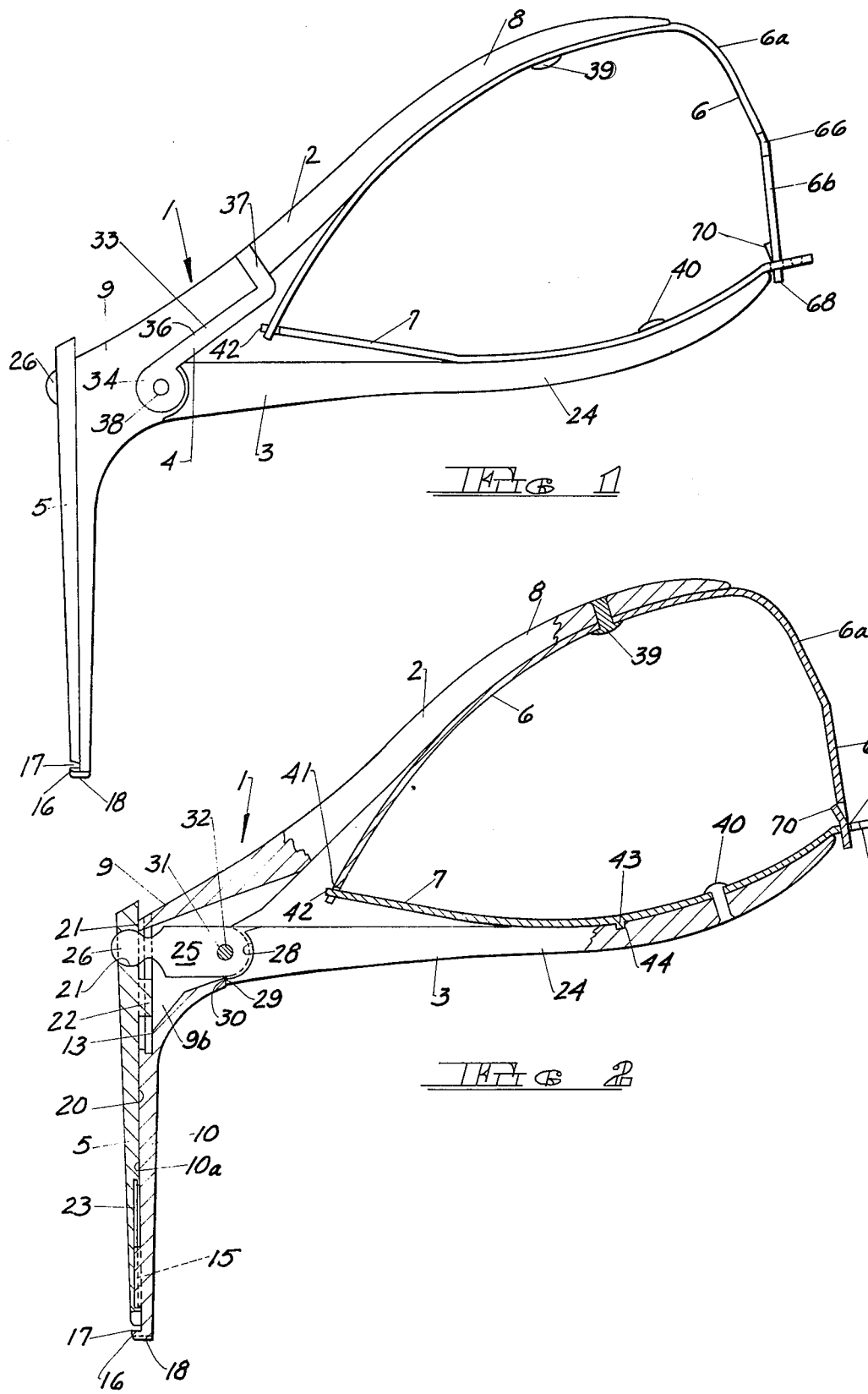

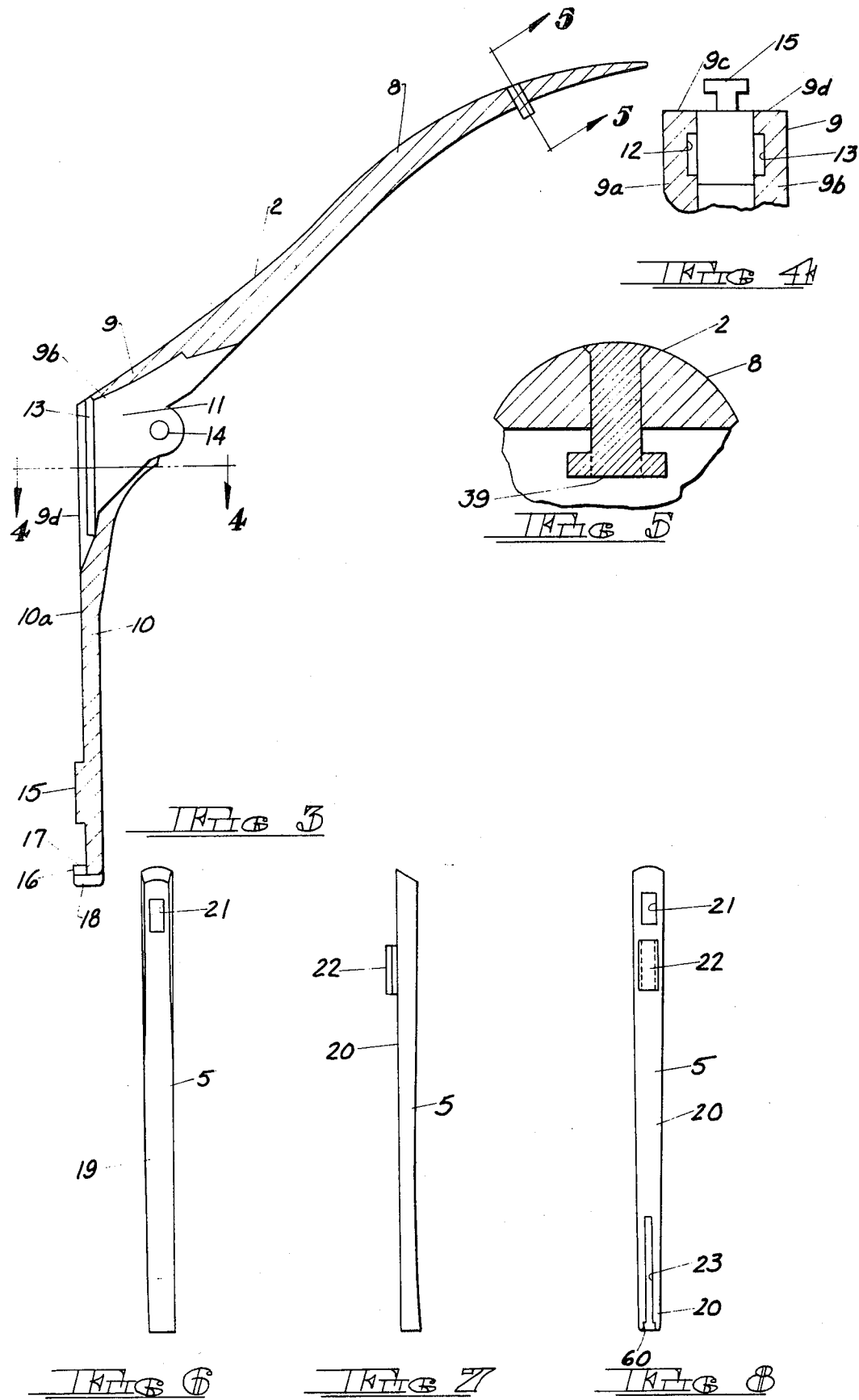

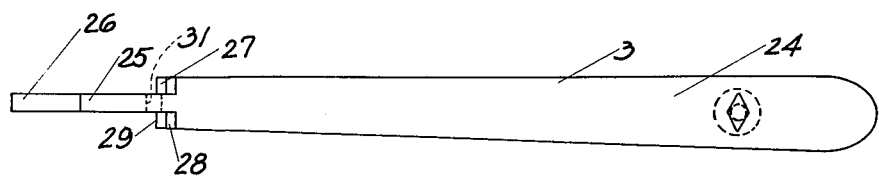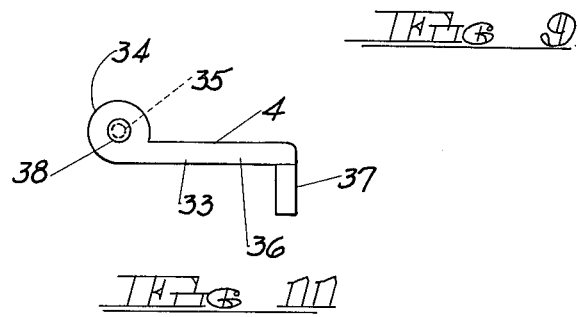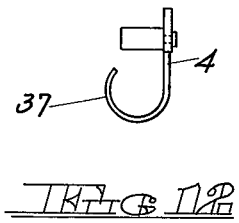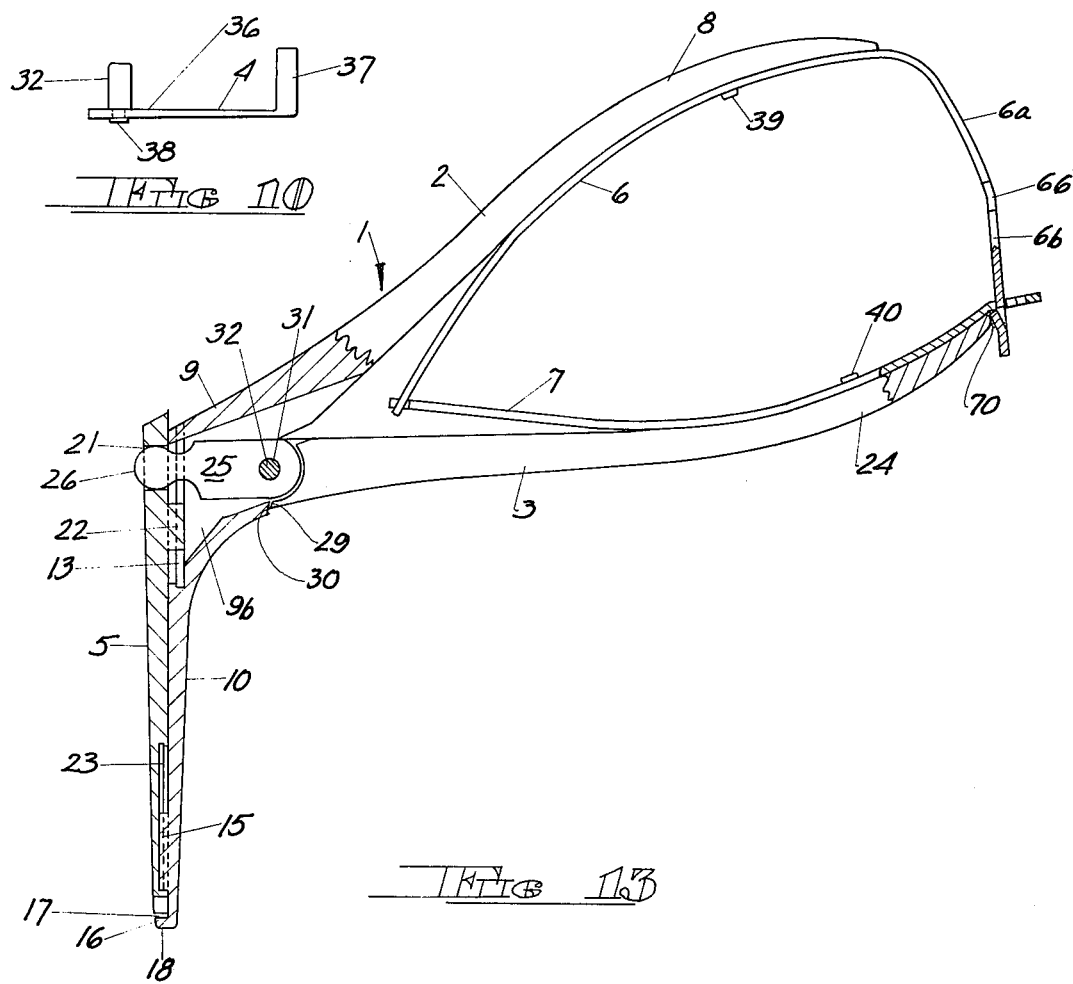

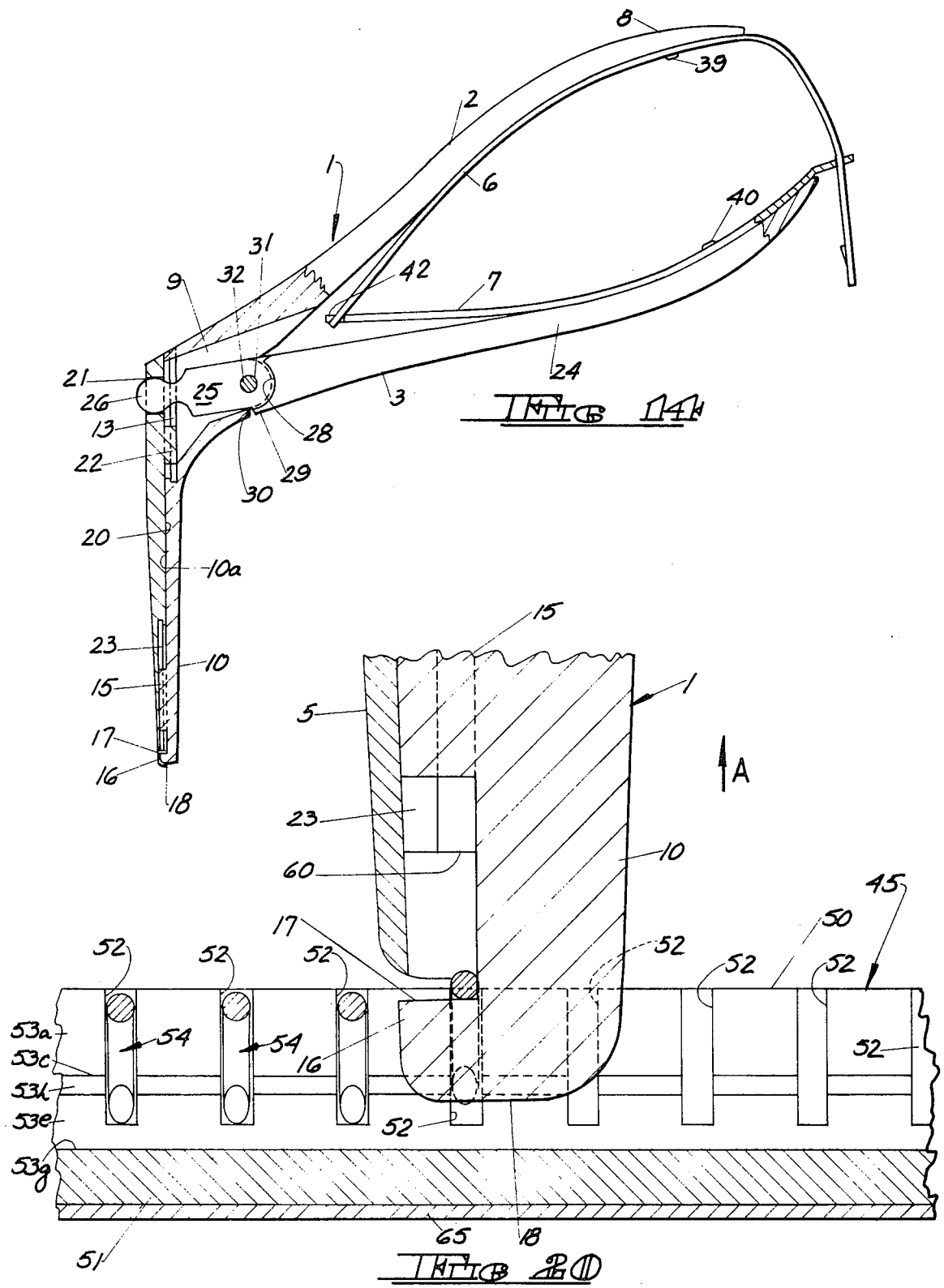

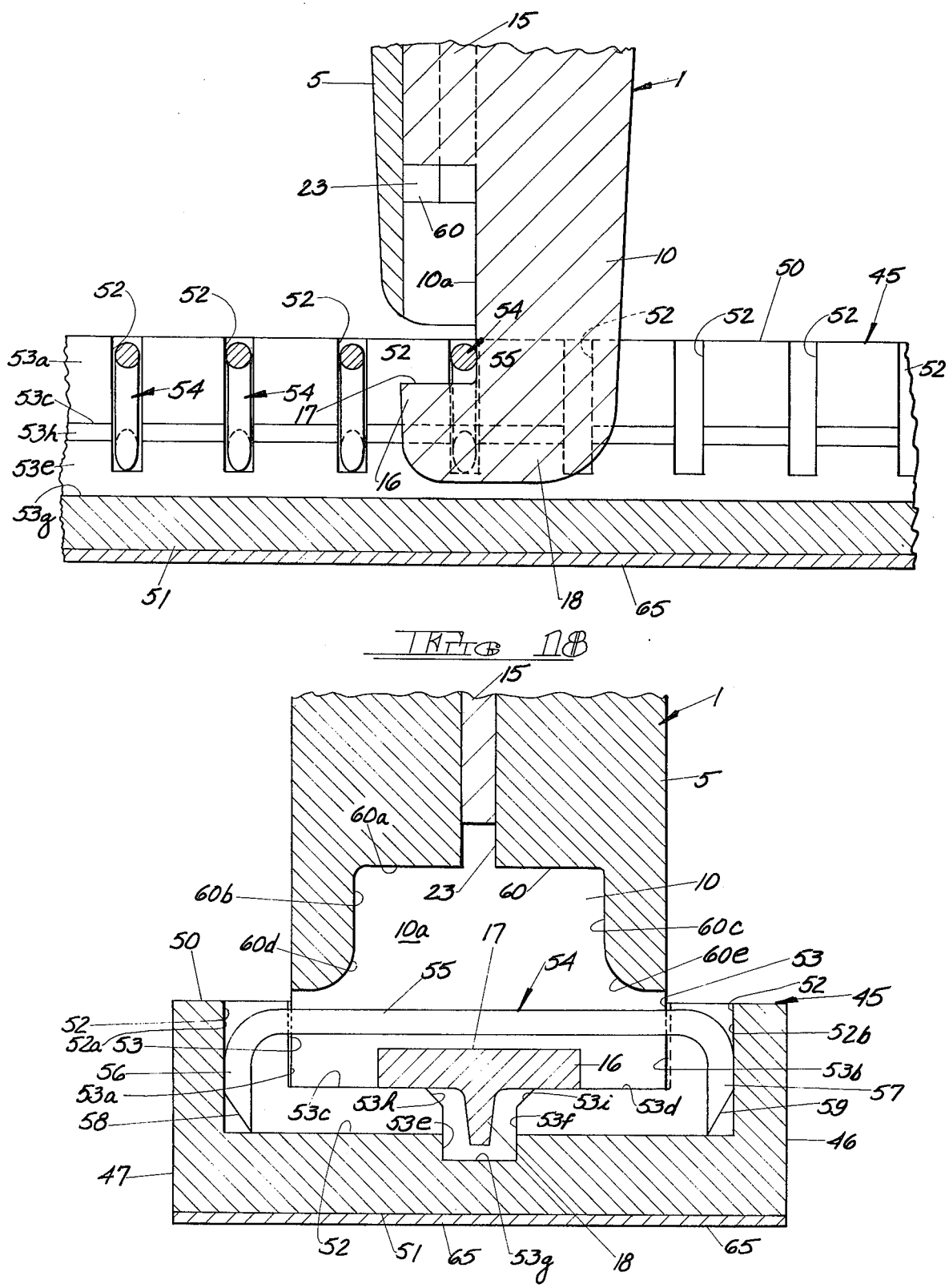

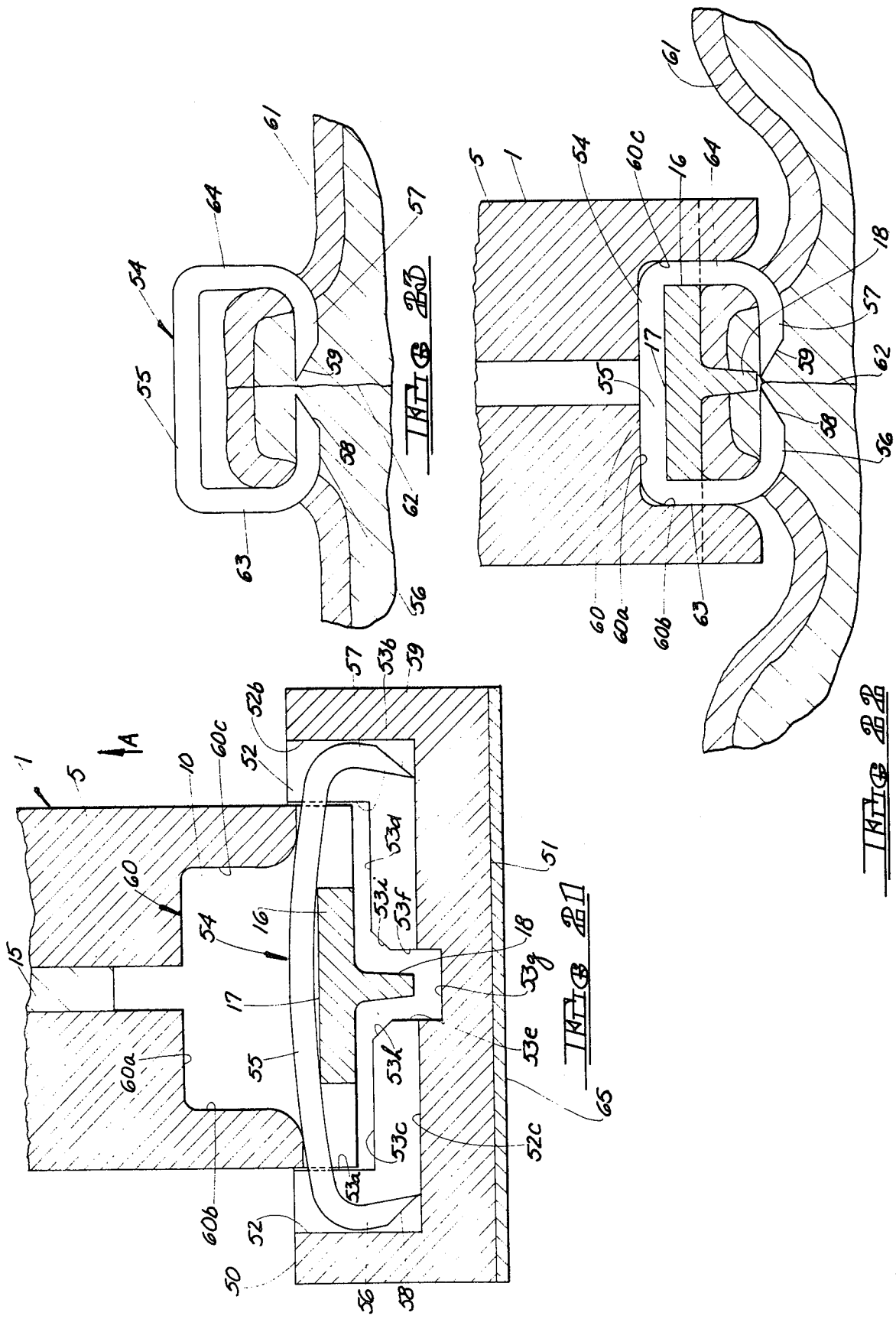

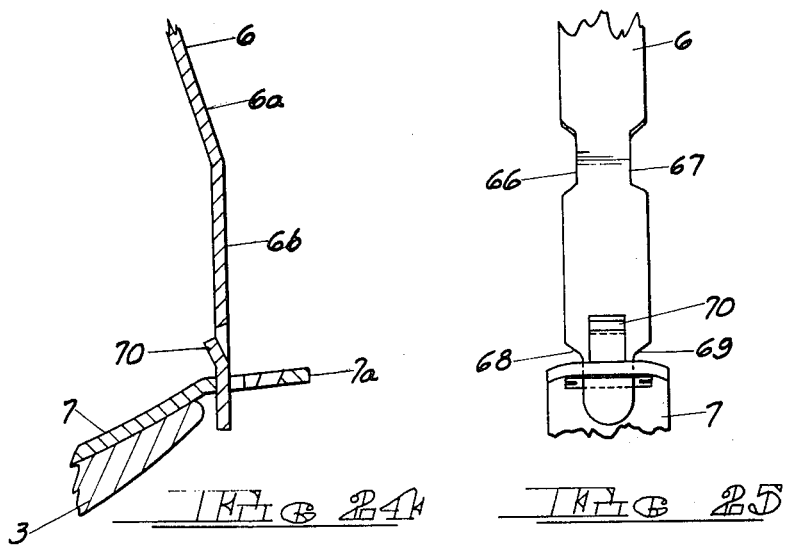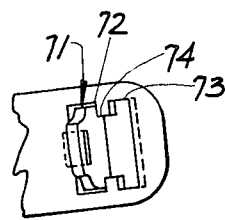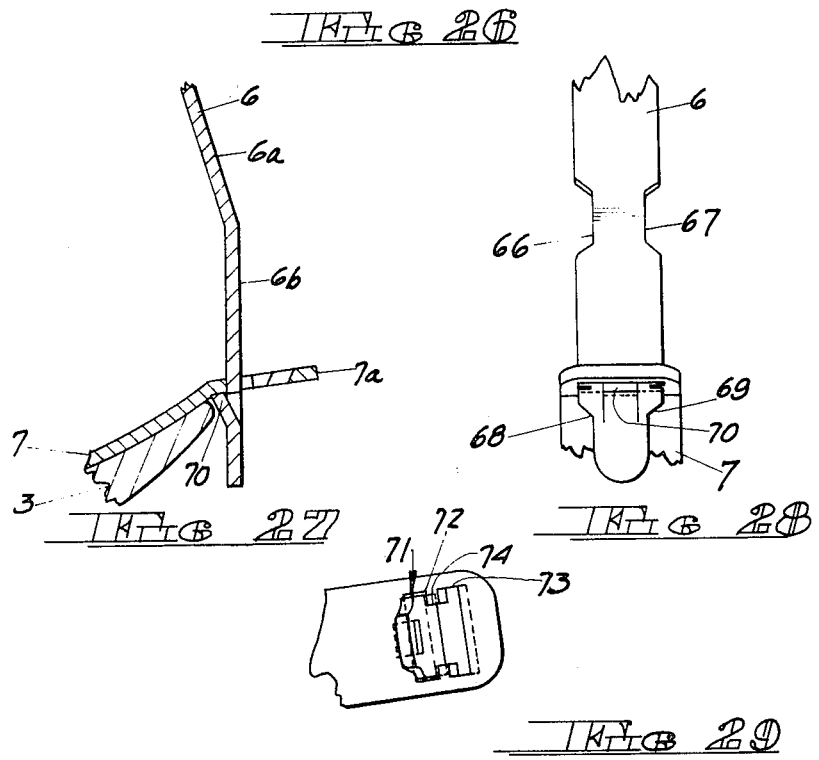

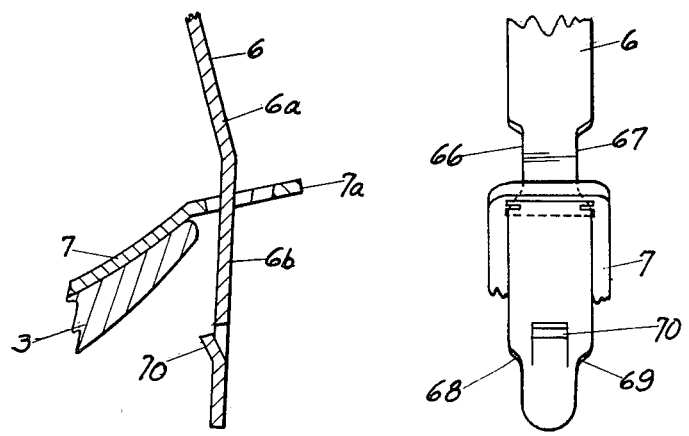
_FIG. 30_  _FIG. 31_
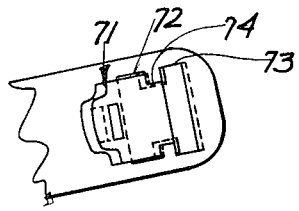
_FIG. 32_
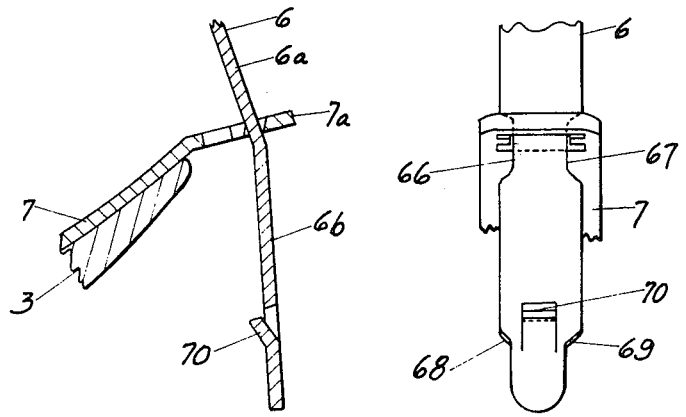
_FIG. 33_  _FIG. 34_
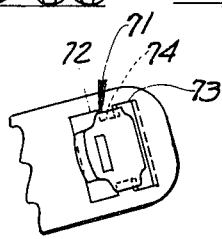
_FIG. 35_

SURGICAL STAPLING INSTRUMENT AND CARTRIDGE THEREFOR

TECHNICAL FIELD

The invention relates to a surgical stapling instrument and cartridge therefor, and more particularly to a pliers-like surgical stapling instrument and a separate one-piece cartridge containing a plurality of staples, each of which may be individually withdrawn from the cartridge by the surgical stapling instrument, to be implanted and formed in the skin or fascia of a patient.

BACKGROUND ART

Recently, surgeons have come more and more to the use of staple sutures, rather than conventional thread sutures, for closing wounds or incisions in the skin or fascia of a patient. This trend is due in part to the fact that the use of staples is a far easier procedure. Of even more importance, however, is that the use of surgical staples is very much faster. This substantially reduces the time required for suturing and the length of time the patient must be maintained under anesthesia.

Prior art workers have devised many types of surgical stapling instruments. Exemplary instruments are taught, for example, in U.S. Pat. No. 3,819,100 and U.S. Pat. No. 4,196,836.

Such surgical stapling instruments have a number of common drawbacks. First of all, they are relatively complicated in construction and design, with a plurality of moving parts. Such instruments, by virtue of their complexity, are subject to jamming, misformed staples and misfed staples. In general, they are bulky at the staple discharge end, thereby obstructing the surgeon's visibility. Their bulkiness and weight in the surgeon's hand may cause excessive fatigue when many staples are required to close a wound or incision.

U.S. Pat. No. 3,278,107 teaches surgical staple applying instruments in the form of a tweezer type instrument and a hemostat type instrument. Both instruments are provided with anvil portions. However, they are of the type wherein the surgical staple is clinched by the anvil portion, rather than formed thereabout.

Prior art workers have also devised numerous hemostatic-type surgical instruments for the application of ligator clips. Exemplary instruments of this type are taught in U.S. Pat. Nos. 3,270,745; 3,326,216; 3,439,523; 3,631,707 and 3,867,944. Instruments of this type, however, are used in a pliers-like fashion to clamp clips about tubular vessels and the like.

Heretofore, prior art workers have developed many types of cartridges for surgical staples. U.S. Pat. No. 3,618,842 teaches a surgical staple cartridge in which the staples are fed by a twin screw arrangement. A ratchet-driven surgical staple cartridge is described in U.S. Pat. No. 3,638,847. In U.S. Pat. No. 3,650,453 a surgical staple cartridge is taught wherein the staples are belt-fed. Finally, in U.S. Pat. No. 4,043,504 there is described a surgical staple cartridge wherein the staples are spring-fed.

These prior art surgical staple cartridges, of which the above noted patents are exemplary only, are generally characterized by complex construction and numerous moving parts. As a result, the opportunity for jamming or misforming of the surgical staples is increased. Such cartridges are normally mounted on the surgical stapling instrument itself. Due to their complex construction and bulkiness they further impede the surgeon's visibility and render it more difficult to accurately locate a surgical staple and see it being formed in the tissue.

Many of the above noted U.S. Patents dealing with instruments for applying ligator clips teach magazines for such clips which are wholly separate from the instruments themselves. Such magazines, however, are not suitable for use with surgical staples since surgical staples must be grasped in a different manner so that they can be clinched about an anvil surface, rather than simply being clamped shut, as in the case of ligator clips.

The above noted U.S. Pat. No. 3,278,107 teaches a surgical staple cartridge wholly separate from the applying instruments. In this instance, however, the cartridge is an elongated rectangular hollow member containing a plurality of spring-advanced capsules or housings, each containing a surgical staple. The stapling instrument engages and removes from the cartridge both a surgical staple and the capsule or housing containing it.

The present invention is directed to a surgical stapling system comprising a surgical stapling instrument and a wholly separate staple-carrying cartridge therefor.

The surgical stapling instrument itself is of very simple six-piece construction. It provides a staple pick-up and locking feature. The instrument is of sturdy, light weight, permanent construction capable of sterilization by any of the well known methods, and is virtually maintenance free. The instrument provides excellent visibility, enabling the entire staple to be seen with the result that accurate placement is very simple to achieve. The instrument cannot jam or misform the staple. The instrument can be completely assembled and disassembled in a matter of seconds without the use of tools. Finally, the instrument is adaptable to many different staple sizes.

The cartridge of the present invention is characterized by a very simple one-piece molded construction. The number of staples to be held in the cartridge is limited only by a practical and convenient length for the cartridge. The design itself is such that the size of staple to be housed in it and the wire size of the staple are not limiting factors.

The cartridge and the staples it contains may be sterilized or resterilized by any of the conventional methods. The cartridge lends itself well to a wide range of pre-sterile packaging.

The one-piece cartridge can be molded of appropriate plastic material in a variety of colors. Thus, the cartridge could be color-coded for quick identification of the size of the staples contained therein. The surgeon can readily ascertain at a glance how many staples remain in the cartridge at any given time. The cartridge may be provided with a pressure sensitive adhesive means on its bottom surface so that it can be removably affixed to any appropriate support, eliminating the necessity for the surgeon to hold the cartridge in his hand during the staple suturing procedure. Alternatively, the bottom of the cartridge may be configured to fit into an appropriate weighted base.

The cartridge of the present invention has means assuring that the anvil portion of the surgical stapling instrument will be properly centered under the crown of each surgical staple. Since the staples are held in place in the cartridge by an interference fit between the outer surfaces of the staple legs and the vertical inner surfaces of the ends of the staple slots, the cartridge can readily be shipped in a filled condition and will, nevertheless, provide for easy and positive removal of the staples from the cartridge. Finally, the cartridge is easily and inexpensively manufactured and, after use, the cartridge provides minimal disposable waste.

DISCLOSURE OF THE INVENTION

According to the invention there is provided a surgical stapling system comprising a surgical stapling instrument and a staple-carrying cartridge therefor. The surgical stapling instrument comprises a pliers-like instrument having first and second handles pivotally joined together. The first handle has an elongated, downwardly depending nose portion which terminates at its lowermost end in an anvil having an anvil surface. A staple former is slidably mounted on the nose portion of the first handle and is axially shiftable therealong by the second handle between a normal or a retracted position and a staple-forming position. Each of the handles has a leaf spring mounted thereon. The leaf springs cooperate to urge the handles apart and bias the former to its normal position. Portions of the leaf springs additionally cooperate to lock the former in a staple gripping position. This enables the instrument to extract a staple from the cartridge and lock it in proper position on the instrument anvil in preparation for forming and implanting in the skin or fascia of the patient.

The surgical staple-carrying cartridge of the present invention comprises a simple, one-piece, integral, elongated member which may be molded of any appropriate plastic material suitable for use in a surgical environment and capable of being sterilized by one or more of the well-known sterilization procedures. The cartridge comprises an elongated, substantially rectangular member having sides, ends, and top and bottom surfaces. A plurality of transversely extending slots are formed in the upper surface of the cartridge in parallel-spaced relationship. The slots are vertically oriented in the cartridge and the ends of each slot are vertical. A conventional surgical staple of inverted U-shaped configuration, having downwardly depending legs and a crown portion extending therebetween, is located in each of the transverse slots. The slots are so sized with respect to the staples that the vertical ends of each slot frictionally engage the legs of the surgical staple located therein. The slots are of such depth that the crowns of the staples located therein are parallel to and spaced slightly below the top surface of the cartridge so as to be wholly contained therein.

The top surface of the cartridge has a groove of T-shaped cross section formed therein. The groove extends longitudinally and centrally of the cartridge throughout its length. The groove is of such width and depth as to receive the anvil portion of the surgical stapling instrument enabling the anvil surface of the instrument to be located beneath the crown of the endmost staple in the cartridge so that the staple can be engaged between the anvil surface and the former and thus extracted from the cartridge by the surgical stapling instrument. The transverse staple-containing slots of the cartridge are so spaced from each other such that each staple may be extracted in its turn from the cartridge without disturbing the next adjacent staple in the cartridge. The longitudinal groove in the cartridge assures that the instrument anvil is centered with respect to the crown of each staple extracted.

BRIEF DESCRIPTION OF THE DRAWINGS

FIG. 1 is a side elevational view of the surgical stapling instrument of the present invention shown in its normal position.

FIG. 2 is a side elevational view, partly in cross section, again showing the instrument in its normal position.

FIG. 3 is a cross sectional view of the first handle of the instrument of FIG. 1.

FIG. 4 is a cross sectional view taken along section line 4—4 of FIG. 3.

FIG. 5 is a cross sectional view taken along section line 5—5 of FIG. 3.

FIG. 6 is a front elevational view of the surgical stapling instrument former.

FIG. 7 is a side elevational view of the former of FIG. 6.

FIG. 8 is a rear elevational view of the former of FIG. 6.

FIG. 9 is a plan view of the second handle of the surgical stapling instrument.

FIG. 10 is a plan view of the pivot pin and keeper assembly of the present invention.

FIG. 11 is a side elevational view of the pivot pin and keeper assembly of FIG. 10.

FIG. 12 is an end elevational view of the pivot pin and keeper assembly, as seen from the right in FIG. 11.

FIG. 13 is an elevational view of the surgical stapling instrument, partly in cross section, illustrating the instrument in its staple pick-up and lock position.

FIG. 14 is a side elevational view of the surgical stapling instrument, partly in cross section, illustrating the instrument in its closed (staple-formed) position.

FIG. 18 is an enlarged elevational view, partly in cross section, illustrating the nose portion of the surgical stapling instrument in position to withdraw a surgical staple from the cartridge.

FIG. 19 is a transverse cross section view of the cartridge, illustrating the nose portion of the surgical stapling instrument in the same position shown in FIG. 18.

FIG. 20 is a fragmentary cross section view, similar to FIG. 18, illustrating engagement of the staple by the surgical stapling instrument between its anvil surface and its former immediately prior to removal of the staple from the cartridge.

FIG. 21 is a fragmentary partial cross sectional view, similar to FIG. 19, illustrating the parts in the same relative position shown in FIG. 20.

FIG. 22 is a fragmentary elevational view, partly in cross section, illustrating the implanting and forming of a surgical staple in the skin or fascia of a patient.

FIG. 23 is a fragmentary elevational view, partly in cross section, illustrating the staple after having been formed and implanted in the skin of a patient.

FIG. 24 is a fragmentary cross sectional elevational view illustrating the locking tab of the spring affixed to the first handle in its normal position within the H-shaped perforation in the spring affixed to the second handle.

FIG. 25 is a fragmentary elevational view of the structure of FIG. 24 as seen from the right of that Figure.

FIG. 26 is a fragmentary bottom view of the structure of FIG. 24.

FIG. 27 is a fragmentary, cross sectional, elevational view, similar to FIG. 24, illustrating the locking tab in locked position.

FIGS. 28 and 29, similar to FIGS. 25 and 26, respectively, illustrate the locking tab in locked position.

FIGS. 30, 31 and 32, equivalent to FIGS. 24, 25 and 26, respectively, illustrate the parts in their relative positions immediately prior to the instrument achieving its fully closed (staple-formed) position shown in FIG. 14.

FIGS. 33, 34 and 35, equivalent to FIGS. 24, 25 and 26, respectively, illustrate the relative position of the parts when the instrument is in its fully closed (staple-formed) position as shown in FIG. 14.

DETAILED DESCRIPTION OF THE INVENTION

Figure 15:
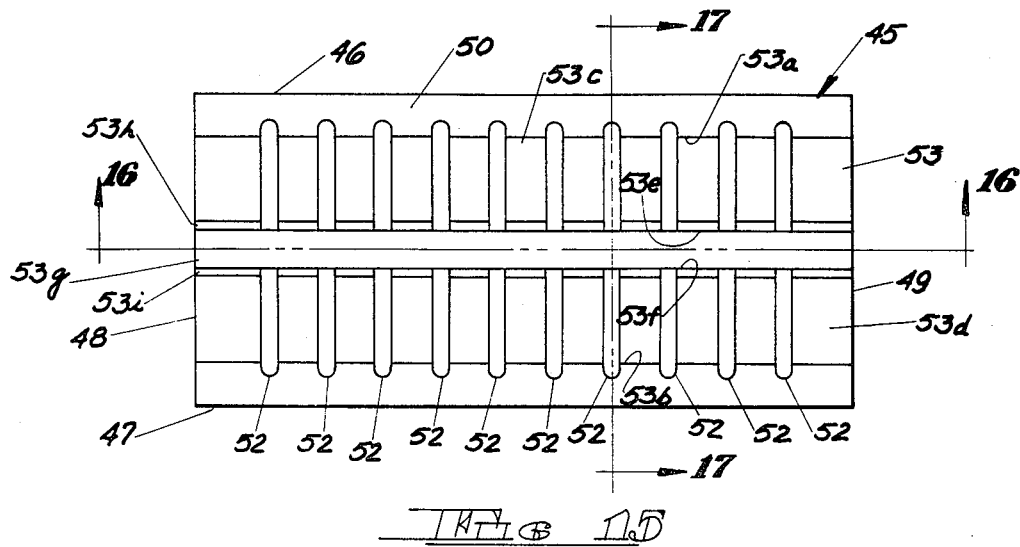
FIG. 15 is a top plan view of the surgical staple cartridge of the present invention.

The surgical stapling system of the present invention comprises a surgical stapling instrument and a staple-carrying cartridge therefor. For purposes of clarity, the surgical stapling instrument will first be described. In all of the Figures, like parts have been given like index numerals.

Reference is first made to FIGS. 1 and 2, wherein the surgical stapling instrument is generally indicated at 1. The surgical stapling instrument is made up of six basic parts: a first or upper handle 2, a second or lower handle 3, a pivot pin and keeper assembly 4, a former 5, an upper spring 6 affixed to the upper handle 2 and a lower spring 7 affixed to the lower handle 3.

Attention is directed also to FIGS. 3 and 4 wherein the upper handle 2 is shown in greater detail. The upper handle 2 has a handle portion 8 adapted to be grasped by the hand of the surgeon, a central body portion 9, and an elongated downwardly depending nose portion 10. The central body portion 9 has a slot 11 extending therethrough, dividing the central portion 9 into two parts or wall portions 9a and 9b in parallel spaced relationship (see FIG. 4). Each of the parts or walls 9a and 9b has a slot formed therein, as shown at 12 and 13, respectively. The slots 12 and 13 extend in the general direction of the nose portion 10, as is evident from FIGS. 3 and 4. The walls 9a and 9b have a pair of coaxial perforations formed therein, one of which is shown at 14 in FIG. 3. These perforations are adapted to receive a pivot pin, as will be described hereinafter.

The elongated nose portion 10 provides a flat forward face 10a which is coextensive with and coplanar with the forward edges 9c and 9d of wall portions 9a and 9b, respectively. Near its lower end, the nose portion 10 is provided with a forwardly extending lug 15 of T-shaped cross section (see FIG. 4).

Nose portion 10 terminates in a forwardly extending anvil 16 having an anvil surface 17 and a downwardly depending flange or keel 18 (see FIGS. 18 and 19), the purpose of which will be described hereinafter.

The former 5 of the surgical stapling instrument is illustrated in FIGS. 6 through 8. The former comprises an elongated member having a front surface 19 and a flat rear surface 20. Near its upper end, the former has a narrow rectangular perforation or window 21, extending from the rear surface 20 through the front surface 19. The purpose of window 21 will be evident hereinafter. Extending rearwardly of surface 20, near the upper end of the former and just below the window 21, there is a lug 22 of T-shaped cross section. The flanges of lug 22 are adapted to be slidably received in the slots 12 and 13 of upper handle 2 (see FIG. 4). Extending from its lowermost end, longitudinally of the former, there is a slot 23 of T-shaped cross section. The slot 23 is adapted to slidably receive the lug 15 on nose portion 10 of upper handle 2. In this fashion, the engagement of former lug 22 in the slots 12 and 13 of upper handle 2 and the engagement of lug 15 of handle 2 in the T-shaped slot 23 of the former enable the former to be removably mounted on the front surface 10a of upper handle 2 and to be shiftable vertically thereon between a normal or retracted position and a lower staple-forming position, as will be further described hereinafter.

The lower or second handle 3 is clearly shown in FIGS. 2 and 9. The lower handle 3 comprises a handle portion 24 adapted to be grasped by the hand of the surgeon. At its forward end, the lower handle 3 terminates in a narrow element 25, the forwardmost portion 26 of which is substantially circular, as seen in FIG. 2. At the juncture of narrow portion 25 and the handle portion 24, the lower handle 3 has a pair of arcuate shoulders 27 and 28 which generally conform to the arcuate configuration of walls 9a and 9b in the area of the pivot pin perforations therein (see FIG. 3). The shoulders 27 and 28 terminate in a transverse stop surface 29. The stop surface 29 cooperates with a similar stop surface 30 on upper handle 2 (see FIG. 2) to determine the openmost position of lower handle 3 (again as is shown in FIG. 2). The portion 25 of lower handle 3 has a transverse perforation 31 therethrough, adapted to receive the pivot pin, as will be described hereinafter.

FIG. 2 illustrates the former 5 mounted on the nose portion 10 of upper handle 2. This Figure also illustrates the lower handle 3 mounted in place. The lower handle 3 is pivotally mounted to upper handle 2 by means of pivot pin 32 which passes through the perforations in upper handle 2 (one of which is shown at 14 in FIG. 3) and the perforation 31 in portion 25 of lower handle 3. It will be noted from FIG. 2 that the circular portion 26 of lower handle 3 is just nicely received in the window 21 of former 5. It will therefore be evident that when lower handle 3 is shifted toward upper handle 2, its circular portion 26 will cause the former 5 to shift from its normal position shown in FIG. 2 downwardly toward anvil 16. When the lower handle 3 returns to its normal position shown in FIG. 2, its circular portion 26 will shift the former 5 to its retracted or normal position, as shown.

The pivot pin and keeper assembly 4 is most clearly illustrated in FIGS. 10 through 12. The keeper comprises a spring metal clip 33. The spring metal clip 33 has a first flat disk-like portion 34 with a central perforation 35 therethrough. The disk-like portion 34 has a laterally extending arm portion 36 which terminates in a transversely extending hook-like portion 37. One end of pivot pin 32 is of lesser diameter and is adapted to extend through the perforation 35 in the disk-like portion 34 of the clip 33. That portion extending through perforation 35 is riveted as at 38 to permanently affix pivot pin 32 to the clip 33.

As is most clearly shown in FIG. 1, when lower handle 3 is properly located in upper handle 2 with its perforation 31 aligned with the perforations in upper handle 2 (one of which is shown at 14 in FIG. 3), pivot pin 32 may be caused to enter the aligned perforations to pivotally join lower handle 3 to upper handle 2. Once the pivot pin 32 has been fully seated, the keeper clip 33 may be rotated until its arm portion 36 lies along upper handle 2 and its hook-shaped portion 37 engages upper handle 2 with a snap fit. This arrangement of parts releasably maintains the pivot pin 32 in place.

With lower handle 3 pivotally affixed to upper handle 2, pivoting of lower handle 3 toward and away from upper handle 2 will, as explained above, result in shifting of former 5 between its normal retracted position and its lower staple-forming position. Leaf springs 6 and 7 are provided to bias lower handle 3 to its openmost position as determined by the abutment of stop surface 29 of lower handle 3 against stop surface 30 of upper handle 2 (see FIGS. 1 and 2) and thus bias the former 5 to its retracted or normal position. Leaf spring 6 is removably attached to the underside of upper handle 2. To this end, upper handle 2 is provided with a headed stud 39, the head of which is spaced from the underside of upper handle 2 by a distance substantially equal to the thickness of leaf spring 6 (see FIG. 5). Leaf spring 6 is provided with an elongated, tapered perforation (not shown), a first part of which is so sized as to permit passage of the head of stud 39 therethrough, and a second part of which is of lesser width than the head of stud 39 so that the spring can be releasably engaged by stud 39 and thereby releasably attached to the underside of upper handle 2.

Leaf spring 7 is similarly releasably attached to the upper side of lower handle 3 by means of a headed stud 40 and an elongated perforation in the spring (not shown). At its forwardmost end, leaf spring 6 is provided with a slot 41 (see FIG. 2), while leaf spring 7, at its forwardmost end, is provided with a tongue 42 receivable within the slot 41 of leaf spring 6. This arrangement acts as a hinge and enables leaf springs 6 and 7 to bias handle 3 to its openmost position. In addition, leaf spring 7 has a downwardly depending stud 43 received in a spring aligning hole 44 in the upper.surface of handle 3. This arrangement maintains both leaf spring 7 and leaf spring 6 properly aligned, and prevents rotation of these leaf springs about their respective studs 39 and 40. The rearwardmost ends of leaf springs 6 and 7 may be provided with a locking arrangement, the nature and purpose of which will be described herinafter.

All of the six basic parts of the instrument 1 can be made of stainless steel or other appropriate material suitable for use in a surgical environment and capable of being autoclaved repeatedly by any conventional means. It will be understood from the above description that the instrument can be completely assembled and disassembled in seconds, without the use of tools, for purposes of thorough cleaning. For example, to disassemble the instrument 1 of FIGS. 1 and 2 it is only necessary to remove the detachable leaf springs 6 and 7. The hook-like portion 37 of pivot pin keeper assembly 4 is released from upper handle 2 and rotated in a counter-clockwise direction (as viewed in FIG. 1). At this point pivot pin 32 can be removed from handles 2 and 3, permitting lower handle 3 to be disengaged from upper handle 2 and former 5. Former 5, in turn, can be removed from the body portion 9 and nose portion 10 of upper handle 2 by simply shifting it vertically upward (as viewed in FIG. 1), thereby releasing the T-shaped lug 15 of nose portion 10 from the T-shaped slot 23 of former 5 and at the same time releasing the T-shaped lug 22 of former 5 from slots 12 and 13 in the body portions 9a and 9b of upper handle 2. For purposes of reassembly, these steps are simply reversed.

Figure 16:
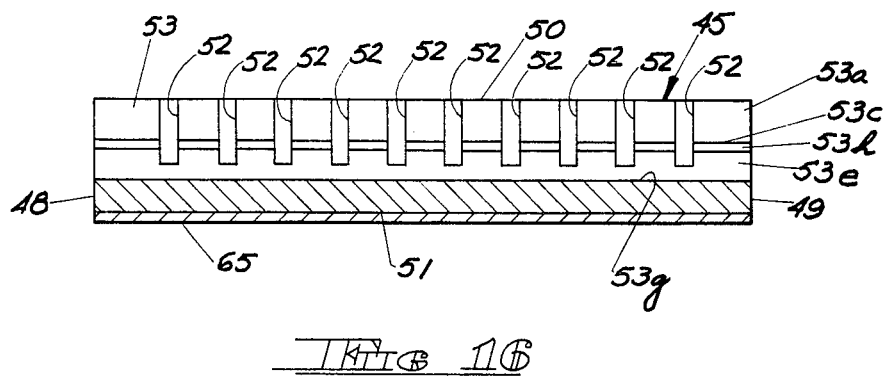
FIG. 16 is a longitudinal cross sectional view taken along section line 16—16 of FIG. 15.
Figure 17:
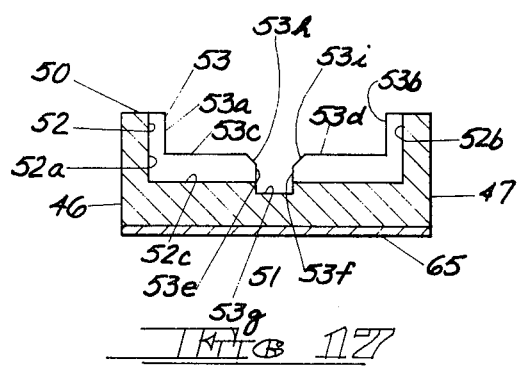
FIG. 17 is a transverse cross sectional view taken along section line 17—17 of FIG. 15.

Reference is now made to FIGS. 15, 16 and 17, which most clearly illustrate the cartridge of the present invention. The cartridge is generally indicated at 45 and comprises a substantially rectangular, elongated member having sides 46 and 47, ends 48 and 49, a top surface 50 and a bottom surface 51. Cartridge 45 is preferably an integral one-piece element molded of plastic material suitable for use in a surgical environment and capable of being sterilized by at least one of the well-known methods. Cartridge 45 is provided with a plurality of identical transverse slots 52. Slots 52 extend downwardly from the top surface 50 of the cartridge and are arranged in parallel spaced relationship. One of the slots 52 is illustrated in FIG. 17. It will be noted that slot 52 has vertically oriented ends 52a and 52b and a horizontal bottom 52c.

Cartridge 45 is also provided with a central longitudinal groove 53, extending the length of the cartridge. As can most easily be seen in FIG. 17, the longitudinal groove 53 has a T-shaped cross section. As a result, groove 53 has upper side walls 53a and 53b, a pair of horizontal surfaces 53c and 53d, a pair of lower side walls 53e and 53f, and a horizontal bottom 53g. The lower side walls 53e and 53f meet horizontal surfaces 53c and 53d in beveled surfaces 53h and 53i, respectively.

FIG. 19 is a Figure similar to FIG. 17 and illustrates a staple located within a transverse slot 52 of cartridge 45. The staple is generally indicated at 54. The staple has a crown portion 55 terminating at its ends in downwardly depending legs 56 and 57. Legs 56 and 57 may be cut on an angle as at 58 and 59, respectively, to render them pointed.

It will be noted from FIG. 19 that slot 52 is of such depth that crown 55 of staple 54 is parallel to and lies just below the top surface 50 of cartridge 45 so that staple 54 is completely contained within the cartridge. Staple 54 is maintained within transverse slot 52 of cartridge 45 by virtue of a frictional engagement between staple legs 56 and 57 and the adjacent vertical ends 52a and 52b of the slot 52.

As will be evident from FIGS. 18 and 19, the lower part of the instrument nose portion 10 is of a width and configuration such as to be just nicely received within the upper portion of cartridge groove 53, defined by groove upper side walls 53a and 53b and groove horizontal surfaces 53c and 53d. The lug or keel 18 of anvil 16 is intended to be received in the lower portion of the longitudinal cartridge groove 53, as defined by side walls 53e and 53f and horizontal bottom 53g.

As can most clearly be seen in FIGS. 8 and 19, the lower end of staple former 5 (on its rear surface 20 and at the bottom end of T-slot 23) is provided with a staple-forming notch 60. As can best be seen in FIG. 19, notch 60 has an upper horizontal surface 60a, parallel to anvil surface 17 and a pair of vertical surfaces 60b and 60c which are spaced from each other by a distance greater than the width of anvil surface 17 so that portions of the staple 54 can be accommodated therebetween during the staple forming procedure, as will be evident hereinafter. It will be noted in FIG. 19 that the lowermost ends of vertical surfaces 60b and 60c curve downwardly and outwardly as at 60d and 60e, respectively.

The surgical stapling instrument 1 and the cartridge 45 of the present invention having been set forth in detail above, their use may be described as follows. The cartridge 45 will come to the surgeon in filled and sterilized condition. When the staple suture procedure is to be performed, the surgeon need only insert the lower end of instrument nose portion 10 in one end or the other of the longitudinal groove 53 of cartridge 45. The lower end of nose portion 10 is so positioned that anvil surface 17 of anvil 16 is located beneath the crown 55 of the first staple 54 in cartridge 45. As will be evident from FIGS. 15, 16 and 18, the transverse staple-receiving slots 52 are so spaced from each other that when anvil 16 is located beneath the crown 55 of a staple 54, it will remain spaced from and out of contact with the next succeeding staple in the row. Anvil 16 is shoved beneath staple crown 55 within longitudinal cartridge groove 53 until crown 55 abuts the forward surface 10a of the instrument nose portion 10. Since the lower end of nose portion 10 is just nicely received within the upper portion of longitudinal cartridge groove 53, the surgeon can be assured that anvil 16 and its anvil surface 17 are properly centered beneath staple crown 55.

The surgeon next squeezes handles 2 and 3 of instrument 1, causing handle 3 to shift toward its actuated position by an amount sufficient to cause the lower end of staple former 5 to contact and slightly bend the crown portion 55 of a staple 54. This is illustrated in FIGS. 20 and 21. It will be noted in FIG. 21 that the slight bend imparted to staple crown 55 will cause staple legs 56 and 57 to shift slightly inwardly, releasing them from their frictional engagement with ends 52a and 52b of transverse slot 52 within which staple 54 is located. FIG. 21 illustrates the lower end of nose portion 10 of surgical stapling instrument 1 as it is being lifted out of cartridge 45 in the direction of arrow A. The same is true of FIG. 20. When the surgical stapling instrument 1 grasps staple 54 as shown in FIGS. 20 and 21, the surgical staple instrument parts assume the relative positions illustrated in FIG. 13.

With staple 54 in the condition illustrated in FIG. 21, gripped between staple former 5 and the anvil surface 17, the surgeon may use the surgical stapling instrument 1 to lift the staple completely out of cartridge 45 and to transfer it to the wound in the skin or fascia of the patient. Surgical stapling instrument 1 is then centered over the wound with the downwardly depending lug or keel 18 of nose portion 10 extending into the wound. Upper handle 2 may then be completely shifted to its fully actuated position. This causes staple former 5 to move downwardly to its lowermost or staple-forming position.

Reference is now made to FIG. 22, which illustrates a surgical staple 54 in its formed and implanted condition at the point where staple former 5 has achieved its lowermost or staple-forming position. In FIG. 22, a patient's skin is illustrated at 61 having a wound or incision 62 therein. It will be noted that the downwardly depending lug or keel 18 of nose portion 10 is located within wound or incision 62 to prevent overlapping of tissue edges during the surgical stapling procedure. Staple former 5 has achieved its lowermost position with the result that sides 60b and 60c of the staple-forming notch 60 have caused portions 63 and 64, respectively, of staple crown 55 to be bent downwardly about anvil surface 17. As a result, staple legs 56 and 57 have been implanted in the skin 61 of the patient and have achieved a position wherein they are substantially diametrically opposed. When the staple is fully formed and implanted, the parts of surgical stapling instrument 1 achieve the relative positions illustrated in FIG. 14.

When lower handle 3 is permitted to return to its normal position (under the influence of cooperating leaf springs 6 and 7), this will result in the return of staple former 5 to its retracted or normal position, out of engagement with staple 54. Anvil 16 and its anvil surface 17 may then be slipped out from under staple 54, leaving the fully formed and implanted staple in the condition shown in FIG. 23.

At this point, the surgeon may reinsert the lower end of nose portion 10 of surgical stapling instrument 1 into longitudinal groove 53 of cartridge 45 to extract therefrom the next succeeding staple 54 in the same manner just described. The next staple 54 may then be formed and implanted in the manner taught with respect to FIGS. 22 and 23. The procedure may be repeated until wound or incision 62 has been completely sutured.

It will be evident from the description above that cartridge 45 of the present invention is of such nature that the surgeon can alway ascertain at a glance how many staples remain in the cartridge. It will be evident that the cartridge may be made to hold any number of staples, limited only by practical length of the cartridge. By appropriately sizing transverse slots 52, the cartridge can be made to hold any size staple of any wire size. To this end, the cartridge can be molded of colored plastic material, and therefore could be color coded for any appropriate reason, such as to indicate at a glance the size of the staple contained within the cartridge, or the initial number of staples contained within the cartridge.

It is within the scope of the present invention to provide the bottom surface 51 of the cartridge with an adhesive layer, a pressure sensitive adhesive layer, or the like. Such an adhesive layer is illustrated at 65 in FIGS. 16 through 21. Adhesive layer 65 permits the surgeon to temporarily attach cartridge 45 to the back of his hand, to a portion of a patient near the wound being sutured, to a portion of the operating table, or to any other suitable surface. This eliminates the necessity for the surgeon to hold the cartridge in his hand during the surgical stapling procedure. As an alternative, bottom surface 51 of the cartridge could be so configured as to fit in a weighted base (not shown) of stainless steel or some other material suitable for use in a surgical environment.

For purposes of convenience, surgical stapling instrument 1 of the present invention may be provided with a locking system to automatically lock the former in its staple-gripping position illustrated in FIGS. 13, 20 and 21. Thus, once the surgeon has gripped and extracted a staple 54 from cartridge 45, he need not maintain pressure on lower handle 3 while the tissue is approximated to make ready for staple placement. Furthermore, with such a locking system, an assistant could locate a staple on anvil surface 17 of surgical stapling instrument 1 and hand the "loaded" surgical stapling instrument to the surgeon for staple forming and implanting.

To this end, reference is made to FIGS. 1, 24, 25 and 26. As is shown in these Figures, the rearward ends of leaf springs 6 and 7 can be configured to provide the desired locking system.

As is most clearly shown in FIG. 1, leaf spring 6 has a first rearward portion 6a which curves downwardly from the end of upper handle 2. Leaf spring 6 has a second portion 6b, angularly related to portion 6a, and substantially planar.

At the juncture of portions 6a and 6b there is a pair of opposed notches 66 and 67 with the result that the portion of leaf spring 6 located between notches 66 and 67 is of diminished width. Notches 66 and 67 will be referred to hereinafter as the transfer notches. At the free end of the portion 6b of leaf spring 6 a second pair of opposed notches 68 and 69 are provided (hereinafter referred to as reset notches) and resulting in the fact that the endmost portion of leaf spring 6 is of about the same width as that portion lying between transfer notches 66 and 67. Just above reset notches 68 and 69, a locking tab 70 is formed in the spring portion 6b by simply offsetting a part of portion 6b. This is clearly shown, for example, in FIG. 24.

Leaf spring 7 has a substantially planar end portion 7a which extends beyond the end of lower handle 3. Spring portion 7a has an H-shaped perforation formed transversely therein and generally indicated at 71 in FIG. 26. The leg of the H-shaped perforation nearest the end of lower handle 3 is indicated by index numeral 72 and will hereinafter be referred to as the former track. Former track 72 is of a length slightly greater than the maximum width of the portion 6b of leaf spring 6. That leg of H-shaped perforation 71 which is remote from the end of lower handle 3 is indicated by index numeral 73 and will hereinafter be referred to as the by-pass track. By-pass track 73 is of a length equal to the length of former track 72. That portion of H-shaped perforation 71 located between former track 72 and by-pass track 73 is indicated by index numeral 74 and will hereinafter be referred to as the transfer slot. Transfer slot 74 is of a width less than the maximum width of portion 6b of leaf spring 6, but greater than the width of those portions of leaf spring 6 located between transfer notches 66 and 67 and reset notches 68 and 69.

The above described rearward ends of leaf spring 6 and 7 constitute the locking system of the present invention. Their operation may be described as follows. When the surgical stapling instrument 1 is in its normal, unactuated condition, as illustrated in FIGS. 1 and 2, the narrow end of portion 6b of leaf spring 6 located between reset notches 68 and 69 will normally extend into former track 72 of spring portion 7a. The configuration of leaf spring 6 and its portions 6a and 6b is such that the lowermost end of portion 6b is constantly biased toward the end of lower handle 3. This is shown in FIGS. 24, 25 and 26.

When the lowermost end of nose portion 10 of instrument 1 is inserted into cartridge 45 with anvil surface 17 located beneath the crown 55 of a surgical staple 54 (as shown in FIGS. 18 and 19), and when the surgeon or his assistant squeezes lower handle 3 to cause the staple 54 to be grasped between former 5 and anvil surface 17 (as shown in FIGS. 20 and 21), this movement of lower handle 3 will cause locking tab 70 on spring portion 6b to pass through former track 72 and to engage the underside of portion 7a of spring 7. This engagement of spring portion 7a by locking tab 70 will cause the staple to be locked in the position shown in FIGS. 20 and 21 and the surgeon or his assistant need no longer apply pressure to lower handle 3. The relative positions of the parts are clearly illustrated in FIGS. 13, 27, 28 and 29.

During the forming and implanting procedure, as lower handle 3 is rotated about its fixed pivot point, the configuration of leaf spring 6 and its portions 6a and 6b is such that portion 6b will be urged toward the by-pass track 73, but will be trapped in the former track 72 since it cannot pass through the narrower transfer slot 74. As a result, leaf spring 6 will ride the rearward edge of former track 72 as shown in FIGS. 30, 31 and 32. However, when the surgical staple is fully formed and implanted, portion 7a of leaf spring 7 will finally reach the transfer notches 66 and 67 in portion 6b of leaf spring 6. Transfer notches 66 and 67 will enable leaf spring 6 to pass from the former track 72 through transfer slot 74 and into by-pass track 73. This is shown in FIGS. 14, 33, 34 and 35.

After the stapling procedure, when the surgeon releases lower handle 3, spring portion 7a will slide down portion 6b of leaf spring 6 via by-pass track 73. The configuration of leaf spring 6 and its portions 6a and 6b is such that as by-pass track 73 slides down portion 6b, portion 6b will be urged toward former track 72, but will be trapped in by-pass track 73 since it cannot pass through the narrower transfer slot 74. The width of locking tab 70 is such, however, that it can pass through transfer slot 74. As soon as reset notches 68 and 69 enter by-pass track 73, they will permit leaf spring 6 to pass from by-pass track 73 through transfer slot 74 to former track 72. Thus, portion 6b reassumes its normal position illustrated in FIGS. 1, 24, 25 and 26 and is therefore in position for the stapling procedure to be repeated.

In the above description and in the claims, terms such as "downwardly depending", "vertical", "upper handle", "lower handle", "top surface", "bottom surface" and the like are used to describe the instrument and its cartridge in relation to the drawings for purposes of clarity. It will be understood that, in use, the instrument and its cartridge can assume any orientation necessary for the particular suturing procedure being practiced at a given time.

Modifications may be made in the invention without departing from the spirit of it.

What is claimed is:

1. A surgical stapling system comprising a surgical stapling instrument and a separate surgical staple-carrying cartridge therefore, said instrument being pliers-like and having upper and lower handles, said upper handle having at its forward end a body portion terminating in an elongated downwardly depending nose portion, said nose portion terminating at its lower end in a forwardly extending anvil having an upper surface comprising an anvil surface, said nose and body portions of said upper handle having coplanar forward surfaces, a staple former being removably and slidably mounted on said forward surfaces above said anvil surface, said lower handle having a forward end, said lower handle being pivotally connected near its forward end to said body portion of said upper handle, said forward end of said lower handle being operatively connected to said former to shift said former from a normal retracted position through a staple engaging position to a staple forming position adjacent said anvil surface when said lower handle is shifted from its normal position toward said upper handle, and to shift said former from its staple forming position to is normal retracted position when said lower handle is shifted away from said upper handle to its normal position, and means biasing said lower handle and said former to their normal positions, said staple carrying cartridge comprising a one-piece, elongated member having sides, top and bottom surfaces and ends, a plurality of slots formed in said top surface of said cartridge and extending vertically downwardly therefrom, said slots extending transversely of the long axis of said cartridge and being in parallel spaced relationship with respect to each other so as to form a row of said slots along the length of said cartridge, each slot terminating in vertical end surfaces and being so sized as to receive a surgical staple therein of the type having a crown terminating in downwardly depending legs, with said vertical end surfaces of said slot frictionally engaging said downwardly depending staple legs to maintain said staple within said slot, said cartridge having a longitudinal groove in said top surface, said longitudinal groove extending the full length of said cartridge and through said ends thereof, said groove intersecting each of said transverse slots, said longitudinal groove being so configured as to just nicely receive said nose portion of said surgical stapling instrument with said anvil surface below and said staple former above an endmost staple in said row of transverse slots, whereby upon partially shifting said staple former from said normal to said staple engaging position said staple will be engaged by said anvil surface and said former and slightly deformed to release the frictional engagement of said staple legs by said slot end enabling said staple to be withdrawn from said cartridge slot by said surgical stapling instrument.

2. The structure claimed in claim 1 including a surgical staple located in each of said transverse slots.

3. The structure claimed in claim 1 wherein each of said transverse slots is of such a depth that a surgical staple located therein will have its crown portion parallel to and below said top surface of said cartridge.

4. The structure claimed in claim 1 wherein said longitudinal groove is of T-shaped cross section.

5. The structure claimed in claim 1 wherein said cartridge is a molded structure of a plastic material suitable for use in a surgical environment.

6. The structure claimed in claim 1 wherein said transverse slots are so spaced from each other that a staple may be removed from each of said slots without disturbing a staple located in the next succeeding slot.

7. The structure claimed in claim 1 including a pressure sensitive adhesive layer on said bottom surface of said cartridge.

8. The structure claimed in claim 1 including a keel depending downwardly from the underside of said anvil and said lower end of said nose portion, said keel being centered with respect to the underside of said anvil and said lower end of said nose portion and extending front to rear thereof.

9. The structure claimed in claim 1 wherein said body portion of said upper handle has a slot extending therethrough and through said forward surface thereof, said lower handle extending through said slot and being pivotally affixed therein by a pivot pin extending through coaxial perforations in said body portion of said upper handle and in said lower handle, said former having a slot extending therethrough near its upper end, said lower handle forward end being rounded and extending beyond said forward surface of said upper handle body portion and into said slot in said former.

10. The structure claimed in claim 1 wherein said means to bias said lower handle and said former to their normal positions comprise first and second leaf springs each having forward and rearward ends, said first and second leaf springs being removably mounted to the facing surfaces of said upper and lower handles respectively, said forward ends of said first and second leaf spring being detachably interconnected whereby said first and second leaf springs bias said former and said lower handle to their normal positions.

11. The structure claimed in claim 9 including a spring clip to removably maintain said pivot pin in place so that said pivot pin can be removed and said lower handle detached from said upper handle, said spring clip comprising an elongated member lying along said upper handle and having first and second ends, said pivot pin being affixed to said first end of said spring clip, said second end of said spring clip having a transverse hook-like configuration releasably engaging said upper handle with a snap fit.

12. The structure claimed in claim 10 including means to maintain said former and said lower handle in said staple engaging position, said last mentioned means comprising an H-shaped slot formed in and extending transversely of the rearward end of said second leaf spring, said leg of said H-shaped slot nearest said rearward end of said second spring comprising a former slot, said other leg of said H-shaped slot comprising a by-pass slot, said portion of said H-shaped slot joining said by-pass and former slots comprising a transfer slot, said first leaf spring having a rearward portion depending downwardly toward said rearward end of said second leaf spring, said rearward portion of said first leaf spring being slightly narrower than said by-pass and former slots and being wider than said transfer slot, said rearward portion of said first leaf spring having an end portion narrower in width than said transfer slot, an integral locking tab just above said end portion and a pair of opposed transfer notches spaced above said locking tab to form a transfer portion narrower than said transfer slot, said first and second leaf springs being so configured that when said lower handle is in said normal position said narrow end portion of said first leaf spring extends into said former slot of said second leaf spring, when said lower handle and said former are shifted to said staple engaging position said locking tab of said first leaf spring engages said second leaf spring rearward end and maintains said lower handle and said former in their staple engaging positions, when said lower handle and said former are shifted to their staple forming positions said first leaf spring is so configured that it transfer portion shifts through said transfer slot into said by-pass slot of said second leaf spring, and as said lower handle and said former return to their normal positions, said rearward portion of said first leaf spring is so configured as to remain in said by pass slot of said second leaf spring until said narrow end portion of said first leaf spring reaches said by-pass slot at which time it shifts through said transfer slot to said former slot.

13. A surgical stapling instrument for forming and implanting surgical staples in the skin or fascia of a patient, said instrument being pliers-like and comprising upper and lower handles, said upper handle having at its forward end a body portion terminating in an elongated downwardly depending nose portion, said nose portion terminating at its free lower end in a forwardly extending anvil having an upper surface comprising an anvil surface, a keel depending downwardly from the underside of said anvil and said lower end of said nose portion, said keel being centered with respect to the underside of said anvil and said lower end of said nose portion and extending front to rear thereof, said nose and body portions of said upper handle having coplanar forward surfaces above said anvil surface, a staple former being removably and slidably mounted on said forward surfaces above said anvil surface, said lower handle having a forward end, said lower handle being pivotally connected near its forward end to said body portion of said upper handle, said forward end of said lower handle being operatively connected to said former to shift said former from a normal retracted position through a staple engaging position to a staple forming position adjacent said anvil surface when said lower handle is shifted from its normal position toward said upper handle, and to shift said former from its staple-forming position to its normal retracted position when said lower handle is shifted away from said upper handle to its normal position, and means biasing said lower handle and said former to their normal positions.

14. The structure claimed in claim 13 wherein said body portion of said upper handle has a slot extending therethrough and through said forward surface thereof, said lower handle extending through said slot and being pivotally affixed therein by a pivot pin extending through coaxial perforations in said body portion of said upper handle and in said lower handle, said former having a slot extending therethrough near its upper end, said lower handle forward end being rounded and extending beyond said forward surface of said upper handle body portion and into said slot in said former.

15. The structure claimed in claim 13 wherein said means to bias said lower handle and said former to their normal positions comprise first and second leaf springs each having forward and rearward ends, said first and second leaf springs being removably mounted to the facing surfaces of said upper and lower handles respectively, said forward ends of said first and second leaf spring being detachably interconnected whereby said first and second leaf springs bias said former and said lower handle to their normal positions.

16. The structure claimed in claim 14 including a spring clip to removably maintain said pivot pin in place so that said pivot pin can be removed and said lower handle detached from said upper handle, said spring clip comprising an elongated member lying along said upper handle and having first and second ends, said pivot pin being affixed to said first end of said spring clip, said second end of said spring clip having a transverse hook-like configuration releasably engaging said upper handle with a snap fit.

17. The structure claimed in claim 14 wherein said means to bias said lower handle and said former to their normal positions comprise first and second leaf springs each having forward and rearward ends, said first and second leaf springs being removably mounted to the facing surfaces of said upper and lower handles respectively, said forward ends of said first and second leaf spring being detachably interconnected whereby said first and second leaf springs bias said former and said lower handle to their normal positions.

18. The structure claimed in claim 15 including means to maintain said former and said lower handle in said staple engaging position, said last mentioned means comprising an H-shaped slot formed in and extending transversely of the rearward end of said second leaf spring, said leg of said H-shaped slot nearest said rearward end of said second spring comprising a former slot, said other leg of said H-shaped slot comprising a by-pass slot, said portion of said H-shaped slot joining said by-pass and former slots comprising a transfer slot, said first leaf spring having a rearward portion depending downwardly toward said rearward end of said second leaf spring, said rearward portion of said first leaf spring being slightly narrower than said by-pass and former slots and being wider than said transfer slot, said rearward portion of said first leaf spring having an end portion narrower in width than said transfer slot, an integral locking tab just above said end portion and a pair of opposed transfer notches spaced above said locking tab to form a transfer portion narrower than said transfer slot, said first and second leaf springs being so configured that when said lower handle is in said normal position said narrow end portion of said first leaf spring extends into said former slot of said second leaf spring, when said lower handle and said former are shifted to said staple engaging position said locking tab of said first leaf spring engages said second leaf spring rearward end and maintains said lower handle and said former in their staple engaging positions, when said lower handle and said former are shifted to their staple forming positions said first leaf spring is so configured that its transfer portion shifts through said transfer slot into said by-pass slot of said second leaf spring, and as said lower handle and said former return to their normal positions, said rearward portion of said first leaf spring is so configured as to remain in said by-pass slot of said second leaf spring until said narrow end portion of said first leaf spring reaches said by-pass slot at which time it shifts through said transfer slot to said former slot.

19. The structure claimed in claim 17 including means to maintain said former and said lower handle in said staple engaging position, said last mentioned means comprising an H-shaped slot formed in and extending transversely of the reaward end of said second leaf spring, said leg of said H-shaped slot nearest said rearward end of said second spring comprising a former slot, said other leg of said H-shaped slot comprising a by-pass slot, said portion of said H-shaped slot joining said by-pass and former slots comprising a transfer slot, said first leaf spring having a rearward portion depending downwardly toward said rearward end of said second leaf spring, said rearward portion of said first leaf spring being slightly narrower than said by-pass and former slots and being wider than said transfer slot, said rearward portion of said first leaf spring having an end portion narrower in width than said transfer slot, an integral locking tab just above said end portion and a pair of opposed transfer notches spaced above said locking tab to form a transfer portion narrower than said transfer slot, said first and second leaf springs being so configured that when said lower handle is in said normal position said narrow end portion of said first leaf spring extends into said former slot of said second leaf spring, when said lower handle and said former are shifted to said staple engaging position said locking tab of said first leaf spring engages said second leaf spring rearward end and maintains said lower handle and said former in their staple engaging positions, when said lower handle and said former are shifted to their staple forming positions said first leaf spring is so configured that its transfer portion shifts through said transfer slot into said by-pass slot of said second leaf spring, and as said lower handle and said former return to their normal positions, said rearward portion of said first leaf spring is so configured as to remain in said by-pass slot of said second leaf spring until said narrow end portion of said first leaf spring reaches said by-pass slot at which time it shifts through said transfer slot to said former slot.

20. The structure claimed in claim 19 including a spring clip to removably maintain said pivot pin in place so that said pivot pin can be removed and said lower handle detached from said upper handle, said spring clip comprising an elongated member lying along said upper handle and having first and second ends, said pivot pin being affixed to said first end of said spring clip, said second end of said spring clip having a transverse hook-like configuration releasably engaging said upper handle with a snap fit.

21. The structure claimed in claim 20 including a keel depending downwardly from the underside of said anvil and said lower end of said nose portion, said keel being centered with respect to the underside of said anvil and said lower end of said nose portion and extending front to rear thereof.

22. A cartridge to contain surgical staples of the type having an inverted U-shaped configuration with a crown portion terminating at its ends in downwardly depending legs, said cartridge being intended for use with a pliers-like surgical stapling instrument having a nose portion with an anvil surface formed thereon and a staple former shiftable between a normal retracted position and an extended position wherein it forms a staple about said anvil surface during emplacement of said staple in the skin or fascia of a patient, said cartridge comprising an integral, one-piece, elongated member having sides, top and bottom surfaces and ends, a plurality of slots formed in said top surface of said cartridge and extending vertically downwardly therefrom, said slots extending transversely of the long axis of said cartridge and being in parallel spaced relationship with respect to each other so as to form a row of said slots along the length of said cartridge, each slot terminating in vertical end surfaces and being so sized as to receive a surgical staple therein with said vertical end surfaces of said slot frictionally engaging said downwardly depending staple legs to maintain said staple within said slot, said cartridge having a longitudinal groove in said top surface, said longitudinal groove extending the full length of said cartridge and through said ends thereof, said groove intersecting each of said transverse slots, whereby said longitudinal groove just nicely receives said nose portion of said surgical stapling instrument with said anvil surface below and said staple former above an endmost staple in said row of transverse slots, such that upon partially shifting said staple former from said normal toward said extended position said staple will be engaged by said anvil surface and said former and slightly deformed to release the frictional engagement of said staple legs by said slot ends enabling said staple to be withdrawn from said cartridge slot by said surgical stapling instrument.

23. The structure claimed in claim 22 including a surgical staple located in each of said transverse slots.

24. The structure claimed in claim 22 wherein each of said transverse slots is of such a depth that a surgical staple located therein will have its crown portion parallel to and below said top surface of said cartridge.

25. The structure claimed in claim 22 wherein said longitudinal groove is of T-shaped cross section.

26. The structure claimed in claim 22 wherein said cartridge is a molded structure of a plastic material suitable for use in a surgical environment.

27. The structure claimed in claim 22 wherein said transverse slots are so spaced from each other that a staple may be removed from each of said slots without disturbing a staple located in the next succeeding slot.

28. The structure claimed in claim 22 including a pressure sensitive adhesive layer on said bottom surface of said cartridge.

* * * * *